US008084255B2

(12) United States Patent
Xia et al.

(10) Patent No.: US 8,084,255 B2
(45) Date of Patent: *Dec. 27, 2011

(54) STEM CELLS TREATED BY IN VITRO FUCOSYLATION AND METHODS OF USE

(75) Inventors: Lijun Xia, Edmond, OK (US); Rodger P. McEver, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/707,481

(22) Filed: Feb. 17, 2010

(65) Prior Publication Data
US 2010/0150883 A1  Jun. 17, 2010

Related U.S. Application Data

(63) Continuation of application No. 11/448,359, filed on Jun. 7, 2006, now Pat. No. 7,776,591, which is a continuation of application No. 10/769,686, filed on Jan. 30, 2004, now Pat. No. 7,332,334.

(60) Provisional application No. 60/463,788, filed on Apr. 18, 2003.

(51) Int. Cl.
*C12N 5/08* (2006.01)
(52) U.S. Cl. ..................................................... 435/372
(58) Field of Classification Search ........................ None
See application file for complete search history.

(56) References Cited

U.S. PATENT DOCUMENTS

| | | | |
|---|---|---|---|
| 5,004,681 A | 4/1991 | Boyse et al. | |
| 5,192,553 A | 3/1993 | Boyse et al. | |
| 5,858,752 A | 1/1999 | Seed et al. | |
| 6,399,337 B1 | 6/2002 | Taylor et al. | |
| 6,440,110 B2 | 8/2002 | Kuypers et al. | |
| 6,461,835 B1 | 10/2002 | Cummings et al. | |
| 6,485,722 B1 | 11/2002 | McIvor et al. | |
| 7,776,591 B2 * | 8/2010 | Xia et al. | 435/366 |
| 2003/0040607 A1 | 2/2003 | Sackstein et al. | |

FOREIGN PATENT DOCUMENTS

| | | |
|---|---|---|
| EP | 04716880 | 9/2007 |
| WO | WO 96/40881 | 12/1996 |
| WO | WO 00/06704 | 2/2000 |
| WO | WO 2005/017115 A3 | 2/2005 |

OTHER PUBLICATIONS

PCT/US04/06474, Search Report, Dec. 5, 2006.
Frenette et al., "Endothelial selectins and vascular cell adhesion molecule-1 promote hematopoietic progenitor homing to bone marrow", *Proc. Natl. Acad. Sci., USA*, Nov. 1998, vol. 95, pp. 14423-14428, Medical Sciences.
Harris et al., "Collection, separation and cryopreservation of umbilical cord blood for use in transplantation", *Bone Marrow Transplantation*, 1994, vol. 13, pp. 135-143.
Hidalgo et al., "Functional selectin ligands mediating human CD34_+ cell interactions with bone marrow endothelium are enhanced postnatally", *The Journal of Clinical Investigation*, Aug. 2002, vol. 110, No. 4, pp. 559-569.
Kobzdej et al., "Discordant expression of selectin ligands and sialyl Lewis x-related epitopes on murine myeloid cells", *Blood*, Dec. 15, 2002, vol. 100, No. 13, pp. 4485-4494.
Mazo et al., "Hematopoietic Progenitor Cell Rolling in Bone Marrow Microvessels: Parallel Contributions by Endothelial Selectins and Vascular Cell Adhesion Molecule 1", *J. Exp. Med.*, Aug. 3, 1998, vol. 188, No. 3, pp. 465-474.
McEver et al., "Perspectives Series: Cell Adhesion in Vascular Biology", *J. Clin. Invest.*, Aug. 1997, vol. 100, No. 3, pp. 485-492.
Nishihira et al., "The Japanese cord blood bank network experience with cord blood transplantation from unrelated donors for haematological malignancies: an evaluation of graft-versus-host disease prophylaxis", *British Journal of Haematology*, 2003, vol. 120, pp. 516-522.
Ramachandran et al., "Dimerization of a selectin and its ligand stabilizes cell rolling and enhances tether strength in shear flow", *Proc. Natl. Acad. Sci.*, Aug. 28, 2001, vol. 98, No. 18, pp. 10166-10171.
Rocha et al., "Comparison of outcomes of unrelated bone marrow and umbilical cord blood transplants in children with acute leukemia", *Blood*, May 15, 2001, vol. 97, No. 10, pp. 2962-2971.
Stevens et al., "Placental/umbilical cord blood for unrelated-donor bone marrow reconstitution: relevance of nucleated red blood cells", *Blood*, Oct. 1, 2002, vol. 100, No. 7, pp. 2662-2664.
Terstappen et al., "Sequential Generations of Hematopoietic Colonies Derived From Single Nonlineage-Committed CD34$^+$ CD$^-$ Progenitor Cells", *Blood*, Mar. 15, 1991, vol. 77, No. 6, pp. 1218-1227.
Thomas, "History, Current Results, and Research in Marrow Transplantation", *Perspectives in Biology and Medicine*, Winter 1995, vol. 38, No. 2, pp. 230-237.
Wagers et al., "Interleukin 12 and Interleukin 4 Control T Cell Adhesion to Endothelial Selectins through Opposite Effects on α1,3-fucosyltransferase VII Gene Expression", *J. Exp. Med.*, Dec. 21, 1998, vol. 188, No. 12, pp. 2225-2231.
Hidalgo et al.,"Enforced fucosylation of neonatal CD34 $^+$ cells generages selectin ligands that enhance the initial interactions with microvessels but not homing to bone marrow" *Blood*, 2005, vol. 105, No. 2, pp. 567-575.
Katayama et al. "PSGL-1 pariticipates in E-selectin-mediated progenitor homing to bone marrow: evidence for cooperation between E-selectin ligands and $_a$4 integrin" Blood, 2003, vol. 102, No. 6, pp. 2060-2067.

(Continued)

*Primary Examiner* — Michail Belyavskyi
(74) *Attorney, Agent, or Firm* — Dunlap Codding, P.C.

(57) ABSTRACT

A method of in vitro fucosylation of selectin ligands on cord blood-derived hematopoietic stem cells for bone marrow transplantation is disclosed. In this method, an effective amount of an α1,3-fucosyltransferase, e.g., α1,3-fucosyltransferase VI, is used in vitro to treat cord blood-derived hematopoietic stem cells to convert non-functional PSGL-1 or other ligands on the cell surface into functional forms that bind selectins, especially P-selectin or E-selectin. The treated cells have enhanced effectiveness in reconstituting bone marrow in patients in need of such therapy.

12 Claims, 11 Drawing Sheets

(1 of 11 Drawing Sheet(s) Filed in Color)

OTHER PUBLICATIONS

Greenbert et al., "Relationship between selectin-mediated rolling of hematopoietic stem and progenitor cells and progression in hematopoietic development", Blood, pp. 478-486, vol. 95, No. 2, Jan. 15, 2000, XP002450253.

Li et al., "Post-translational Modifications of Recombinant P-selectin Glycoprotein Ligand-1 Required for Binding to P- and E-selectin", *Journal of Biological Chemistry*, pp. 3255-3264, vol. 271, No. 6, Issue of Feb. 6, 1996, XP002116305.

Snapp et al., "P-Selectin Glycoprotein Ligand-1 Is Essential for Adhesion to P-Selectin But Not E-Selectin in Stably Transfected Hematopoietic Cell Lines", *Blood*, vol. 89, No. 3 (Feb. 1, 1997), pp. 896-901.

Da Silva et al., "Differences Amid Bone Marrow and Cord Blood Hematopoietic Stem/Progenitor Cell Division Kinetics", *Journal of Cellular Physiology*, published online Mar. 10, 2009, Wiley InterScience (www.interscience.wiley.com), PP. 102-111.

Grewel et al., "Unrelated donor hematopoietic cell transplantation: marrow or umbilical cord blood?" *Blood*, Jun. 1, 2003, vol. 101, No. 11, pp. 4233-4244.

Hao et al., "A functional comparison of CD34 + CD38 cells in cord blood and bone marrow" *Blood*, Nov. 15, 1995, vol. 86, No. 10, pp. 3745-3753.

Rini et al., "Glycosyltransferases and Glycan-processing Enzymes" *Essentials of Glycobiology*, Second Edition, published by Cold Spring Harbor Laboratory Press, cold Spring Harbor, New York, 2009 by The Consortium of Glycobiology Editors, La Jolla, California, pp. 63-73.

Theunissen et al., "A multifactorial analysis of umbilical cord blood, adult bone marrow and mobilized peripheral blood progenitors using the improved ML-IC assay" *Experimental Hematology*, vol. 33 (2005) pp. 165-172.

Van Den Oudenrigin et al., "Differences in megakaryocyte expansion potential between CD34[+] stem cells derived from cord blood, peripheral blood, and bone marrow from adults and children" *Experimental Hematology*, vol. 28 (2000) pp. 1054-1061.

Yasui, et al., "Differences Between Peripheral Blood and Cord Blood in the Kinetics of Lineage-Restricted Hematopoietic Cells: Implications for Delayed Platelet Recovery Following Cord Blood Transplantation" *Stem Cells* vol. 21 (2003) pp. 143-151.

Xia et al., European Patent Application No. 04716880.2-2405, "Hematopoietic Stem Cells Treated by In Vitro Fucosylation and Methods of Use" Office Action mailed Mar. 28, 2008, 6 pgs.

Xia et al., European Patent Application No. 04716880.2-2405, "Hematopoietic Stem Cells Treated by In Vitro Fucosylation and Methods of Use" Response mailed Oct. 7, 2008, 9 pgs.

Xia et al., European Patent Application No. 04716880.2-2405, "Hematopoietic Stem Cells Treated by In Vitro Fucosylation and Methods of Use" Office Action mailed Nov. 25, 2008, 4 pgs.

Xia et al., European Patent Application No. 04716880.2-2405, "Hematopoietic Stem Cells Treated by In Vitro Fucosylation and Methods of Use" Response mailed Jun. 5, 2009, 4 pgs.

Xia et al., European Patent Application No. 04716880.2-2405, "Hematopoietic Stem Cells Treated by In Vitro Fucosylation and Methods of Use" Office Action mailed Aug. 3, 2009, 6 pgs.

Xia et al., European Patent Application No. 04716880.2-2405, "Hematopoietic Stem Cells Treated by In Vitro Fucosylation and Methods of Use" Response mailed Feb. 9, 2010, 7 pgs.

Xia et al., Japanese Patent Application No. 2006-509036, "Hematopoietic Stem Cells Treated by In Vitro Fucosylation and Methods of Use" Office Action mailed Dec. 28. 2009 5 pgs (2 pgs in Japanese; 3 pgs in English Translation).

* cited by examiner

US 8,084,255 B2

STEM CELLS TREATED BY IN VITRO FUCOSYLATION AND METHODS OF USE

CROSS REFERENCE TO RELATED APPLICATIONS

This application is a continuation of U.S. Ser. No. 11/448,359, filed Jun. 7, 2006, now U.S. Pat. No. 7,776,591, which is a continuation of U.S. Ser. No. 10/769,686, filed Jan. 30, 2004, now U.S. Pat. No. 7,332,334, which claims the benefit under 35 U.S.C. 119(e) of U.S. Provisional Application Ser. No. 60/463,788, filed Apr. 18, 2003, each of which is hereby expressly incorporated by reference herein in its entirety.

STATEMENT REGARDING FEDERALLY SPONSORED RESEARCH OR DEVELOPMENT

This invention was made with government support under Grant 5P5OHL54502 awarded by the National Institutes of Health. The Government has certain rights in the invention.

BACKGROUND OF THE INVENTION

This invention generally relates to methods of treating hematopoietic stem cells (HSCs) for improving their therapeutic usefulness and more particularly, but not limited to, treating hematopoietic stem cells derived from cord blood, and hematopoietic stem cells thus treated.

During inflammation, P-selectin and E-selectin cooperatively mediate leukocyte rolling and adhesion on vascular surfaces (McEver, R. P. Selectins: lectins that initiate cell adhesion under flow. Curr Opin Cell Biol. 2002 October; 14:581-856). In the process of bone marrow transplantation, P-selectin and E-selectin also mediate the homing of intravenously injected HSCs to bone marrow. (Frenette, P. S., Subbarao, S., Mazo, I. B., Von Andrian, U. H., Wagner, D. D. Endothelial selectins and vascular cell adhesion molecule-1 promote hematopoietic progenitor homing to bone marrow. Proc. Natl. Acad. Sci. USA. 1998; 95:14423-14428). In most tissues, P-selectin and E-selectin are expressed on endothelial cells after stimulation of agonists, but they are expressed constitutively on bone marrow endothelial cells. Selectins use $\alpha 2,3$-sialylated and $\alpha 1,3$-fucosylated glycans such as sialyl Lewis$^x$ (sLe$^x$) on glycoproteins or glycolipids as ligands. P-selectin binds to the N-terminal region of P-selectin glycoprotein ligand-1 (PSGL-1), which contains tyrosine sulfates and an O-glycan capped with sLe$^x$. E-selectin binds to one or more different sites on PSGL-1. To interact with E-selectin, PSGL-1 does not require tyrosine sulfation, but expression of sLe$^x$ on O-glycans enhances binding. E-selectin also interacts with other ligands on HSCs. An isoform of CD44 on HSCs has been shown to bind to E-selectin in vitro (Dimitroff, C. J., Lee, J. Y., Rafii, S., Fuhlbrigge, R. C., Sackstein, R. CD44 is a major E-selectin ligand on human hematopoietic progenitor cells. J. Cell Biol. Jun. 11, 2001; 153:1277-1286). Another potential ligand for E-selectin on HSCs is E-selectin ligand-1 (ESL-1) (Wild, M. K., Huang, M. C., Schulze-Horsel, U., van Der Merwe, P. A., Vestweber, D. Affinity, kinetics, and thermodynamics of E-selectin binding to E-selectin ligand-1. J Biol. Chem. 2001 Aug. 24; 276:31602-31612). Each of these glycoprotein ligands is thought to carry sLe$^x$ structures.

Hematopoietic stem cells harvested from one individual can be transplanted to the bone marrow of another individual following an intravenous infusion. The approach has been widely used in treatment of various hematological disorders such as leukemia (Thomas, E. D. History, current results, and research in marrow transplantation. Perspectives Biol. Med. 38:230-237.1995). Clinically, human HSCs are obtained from three different sources: bone marrow, adult peripheral blood after mobilization, and cord blood obtained from umbilical cords after delivery. Although there are more than 5 million unrelated bone marrow volunteer donors registered worldwide, finding a fully human leukocyte antigen (HLA)-matched unrelated donor remains a problem for many patients because of HLA polymorphism. Compared with bone marrow and adult peripheral blood, cord blood has several potential advantages, in particular the wide and rapid availability of cells and less stringent requirements for HLA identity between donor and recipient because of the lower risk of acute and chronic graft-versus-host disease (GVHD) (Rocha, V., et. al., Comparison of outcomes of unrelated bone marrow and umbilical cord blood transplants in children with acute leukemia. Blood. 97:2962-71.2001). Potential advantages of transplantation using cord blood HSCs rather than HSCs from bone marrow or adult peripheral blood include: (1) a large potential donor pool; (2) rapid availability, since the cord blood has been prescreened and tested; (3) greater racial diversity can be attained in the banks by focusing collection efforts on hospitals where children of under represented ethnic backgrounds are born; (4) reduced risk or discomfort for the donor; (5) rare contamination by viruses; and (6) lower risk of graft-versus-host disease (wherein the donor's cells attack the patient's organs and tissues), even for recipients with a less-than-perfect tissue match. Thus, cord blood-derived HSCs have been increasingly used for bone marrow transplantation in recent years.

In the transplantation setting, the intravenously infused HSCs specifically extravasate in the bone marrow to engraft and proliferate, a process that is defined as HSC homing. Homing has been studied extensively both in vivo and in vitro and is believed to rely on adhesion molecule interactions between HSCs and endothelium of bone marrow. Selectins are a group of adhesion molecules containing a N-terminal carbohydrate-recognition domain related to those in Ca$^{++}$-dependent (C-type) animal lectins. P-selectin, expressed on activated platelets and endothelial cells, and E-selectin, expressed on activated endothelial cells, bind to glycoconjugate ligands on leukocytes and HSCs. The best-characterized glycoprotein ligand is PSGL-1, a mucin with many sialylated and fucosylated O-linked oligosaccharides. PSGL-1 is expressed on leukocytes and HSCs. Studies with PSGL-1-deficient mice have shown that PSGL-1 mediates leukocyte tethering to and rolling on P-selectin and supports tethering to E-selectin in flow. PSGL-1 also binds to L-selectin, which initiates leukocyte-leukocyte interactions that amplify leukocyte rolling on inflamed endothelial cell surfaces. In human PSGL-1, the P-selectin and L-selectin binding site comprises a peptide sequence containing three tyrosine sulfate residues near a threonine to which is attached a specific branched, fucosylated core-2 O-glycan (McEver, R. P., Cummings, R. D. Role of PSGL-1 binding to selectins in leukocyte recruitment. J Clin Invest. 100:S97-103. 1997; R. P. McEver: Selectins: Ligands that initiate cell adhesion under flow. Curr. Op. in Cell Biol. 14: 581-586, 2002). The fucose moiety is essential for P-selectin binding as measured by in vitro assays using synthetic glycosulfopeptides. The fucosylation is catalyzed by a family of $\alpha 1,3$-fucosyltransferases. Among them, $\alpha 1,3$-fucosyltransferase IV (FT-IV) and $\alpha 1,3$-fucosyltransferase VII (FT-VII) are primarily expressed in human leukocytes. These enzymes catalyze the transfer of a fucose residue from a donor, e.g., GDP-fucose, to an acceptor in $\alpha 1,3$-linkage to GlcNAc in Gal-GlcNAc-sequences. Both FT-IV and FT-VII make the fucose addition which is necessary to form the sLe$^x$ structure (NeuAc$\alpha 2,3$Gal$\beta 1,4$[Fuc$\alpha 1,3$]GlcNAc$\beta 1$-R). The sLe$^x$ on a core-2 O-glycan attached to a specific threonine in the N-terminal amino acid sequence of human PSGL-1 is critical for binding to P-selectin.

HSCs have the potential to differentiate into different lineages of hematopoietic cells such as red blood cells, myeloid cells, lymphocytes and platelets. Human HSCs express a surface glycoprotein, CD34, which is routinely used for HSC identification and separation. Such human CD34$^+$ cells (cells which express CD34 antigen) represent a heterogeneous population of progenitors with various degrees of hematopoietic maturation. The absence of ("−") or reduced ("low") expression of another surface protein, CD38, on human CD34$^+$ cells is considered to be a surrogate marker of a primitive subpopulation of CD34$^+$ cells. Thus, the cells of the CD34$^+$CD38$^{low/-}$-sub-population, which comprise approximately 10-20% of the total CD34$^+$ cells from bone marrow or adult peripheral blood, are highly enriched for multiprogenitor and stem cell activity, including engraftment ability. Notably, approximately 30% of cord blood HSCs are CD34$^+$CD38$^{low/-}$. However, unlike CD34$^+$CD38$^{low/-}$ adult peripheral blood stem cells, cord blood CD34$^+$CD38$^{low/-}$ HSCs are known to have reduced homing to murine bone marrow, which is primarily dependent on interactions of human HSCs with murine P-selectin on the microvascular endothelium (Hidalgo, A., Weiss, L. A., and Frenette, P. S. Functional selectin ligands mediating human CD34$^+$ cell interaction with bone marrow endothelium are enhanced postnatally. Adhesion pathways mediating hematopoietic progenitor cell homing to bone marrow. J. Clin. Invest. 110: 559-569. 2002). Flow cytometry analyses indicate that this homing defect results from non-functional PSGL-1 expressed on these CD34$^+$CD38$^{low/-}$ cord-blood derived HSCs. Thus, the impaired ability of the CD34$^+$CD38$^{low/-}$ HSCs to bind to P-selectin explains in at least in part the delayed platelet and myeloid engraftment associated with cord blood HSC transplantation. The use of cord blood HSCs for transplantation has been primarily restricted to children (which require fewer cells for transplantation) due to the limited quantities and defective homing ability of HSCs isolated from umbilical cords.

An invention which corrects the homing defect of HSCs would significantly increase the potential of umbilical cord blood as a source of hematopoietic stem cells and would thereby lead to lower risks for acute and chronic graft-versus-host disease and improved success of bone marrow reconstitution.

SUMMARY OF THE INVENTION

The present invention in one embodiment contemplates a method of treating HSCs comprising the steps of providing a quantity or population of HSCs, at least some of which lack or have reduced expression of surface protein CD38, and treating the quantity or population of HSCs in vitro with an α1,3 fucosyltransferase and a fucose donor, wherein the treated HSCs have enhanced binding to P-selectin and E-selectin. Furthermore, the HSCs are typically characterized as comprising P-selectin glycoprotein ligand-1 (PSGL-1) and/or other selectin ligands which does not effectively bind to P-selectin or E-selectin. More particularly, the PSGL-1 or other selectin ligands which occurs on the CD34$^+$ CD38$^{low/-}$ HSCs lack, or have fewer, fucosylated glycans, particularly O-glycans, and may for example, have PSGL-1 which have core-2 O-glycans which comprise NeuAcα2,3Galβ1,4GlcNAc and which lack fucose in α1,3 linkage to the GlcNAc. The HSCs, in their untreated state prior to fucosylation as described herein, have reduced bone marrow homing ability. In one embodiment of the invention, the HSCs are derived from human umbilical cord blood, though they may be derived from bone marrow or peripheral blood, as long as they are characterized as having enhanced bone marrow homing ability after the fucosylation treatment. In the method contemplated herein, the α1,3 fucosyltransferase may be, for example, an α1,3 fucosyltransferase IV, an α1,3 fucosyltransferase VI, or an α1,3 fucosyltransferase VII, or a combination thereof. The fucose donor may be, for example, GDP-fucose.

The invention further contemplates in one embodiment a composition of treated human HSCs which comprise cord blood-derived CD34$^+$ HSCs lacking or having reduced expression of surface protein CD38 (CD38$^{low/-}$), wherein the HSCs are able to bind to P-selectin or E-selectin. The HSCs may be disposed in a pharmaceutically acceptable carrier, or diluent, or vehicle for storage or administration to a patient. The invention is further directed to a treatment method, comprising administering an effective amount of the HSCs to a subject having a hematological disorder or other disease requiring or benefiting from a transplantation of HSCs for treatment.

As noted above, after the fucosylation treatment described herein, the treated CD34$^+$ HSCs (including CD34$^+$CD38$^{low/-}$ HSCs) have enhanced binding to P-selectin or E-selectin, as compared to untreated CD34$^+$ HSCs. Enhanced binding to P-selectin (or E-selectin) is defined as at least 10% of the treated HSCs having fluorescence in a P-selectin (or E-selectin, respectively) binding assay which is greater than a predetermined fluorescence threshold (as defined below). In another embodiment, at least 25% of the treated HSCs exceed the predetermined fluorescence threshold. In another embodiment, at least 50% of the treated HSCs exceed the predetermined fluorescence threshold. In another embodiment, at least 75% of the treated HSCs exceed the predetermined fluorescence threshold. In another embodiment, at least 90% of the treated HSCs exceed the predetermined fluorescence threshold. In another embodiment, at least 95% of the treated HSCs exceed the predetermined fluorescence threshold.

The present invention further contemplates a blood product produced by the method including the steps of providing a quantity or population of HSCs, at least a portion of which are CD34$^+$ and which lack or have reduced expression of protein CD38, and treating the quantity of HSCs in vitro with an α1,3 fucosyltransferase and a fucose donor, wherein the majority of the treated HSCs have enhanced binding to P-selectin (or E-selectin) as described herein. The quantity of HSCs are preferably derived from umbilical cord blood but may be obtained from bone marrow or adult peripheral blood. The quantity or population of HSCs could comprise a portion, or unfractionated sample, of blood or bone marrow.

BRIEF DESCRIPTION OF THE FIGURES

This patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
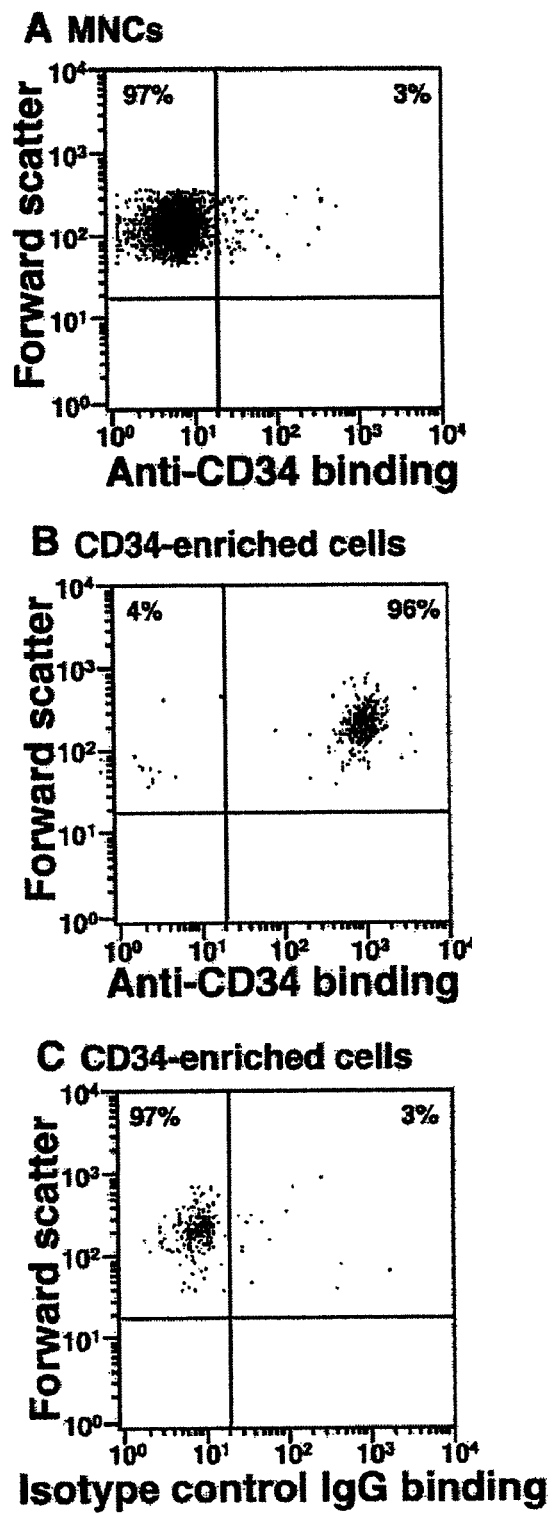
FIG. 1. A. CD34 antibody staining of mononuclear cells (MNCs) isolated from human cord blood. B. CD34 antibody staining of cells after CD34-enrichment. C. Isotope control IgG staining of CD34$^+$ cells. Axes are fluorescence intensity as measured by flow cytometry.

The present invention in one embodiment contemplates a method of treating HSCs comprising providing a quantity or population of HSCs which lack or have reduced expression (less than the normal level of expression of CD38) of surface protein CD38, and treating the quantity or population of HSCs in vitro with an α1,3 fucosyltransferase and a fucose donor, wherein the HSCs so treated have enhanced binding to P-selectin or E-selectin over the untreated HSCs. Furthermore, the untreated HSCs are typically characterized as predominantly comprising PSGL-1 or other selectin ligands which do not adequately bind to P-selectin or E-selectin. The PSGL-1 or other selectin ligands which occur on the CD38$^{low/-}$ HSCs lack or have reduced numbers of fucosylated glycans, such as O-glycans, and may for example, have PSGL-1 which have core-2 O-glycans which comprise NeuAcα2,3Galβ1,4GlcNAc but which lack a fucose in α1,3 linkage to the GlcNAc. The CD38$^{low/-}$ HSCs, in their untreated state prior to fucosylation, have reduced bone marrow homing ability. Preferably, the HSCs are derived from human umbilical cord blood (CB), although they may be derived from bone marrow or peripheral blood, as long as they are characterized as needing, or benefiting from, further fucosylation to enhance their bone marrow homing ability. In the method contemplated herein, the α1,3 fucosyltransferase may be for example α1,3 fucosyltransferase IV, α1,3 fucosyltransferase VI, or α1,3 fucosyltransferase VII. The fucose donor may be for example GDP-fucose.

The invention contemplates in one embodiment a composition of treated human HSCs which comprise cord blood-derived HSCs lacking or having reduced expression of surface protein CD38 (CD38$^{low/-}$), wherein the treated HSCs comprise PSGL-1 or other selectin ligands that are properly fucosylated (e.g., comprises sialyl Lewis$^x$) and which are able to bind to P-selectin (or E-selectin). The treated HSCs may be disposed in a pharmaceutically acceptable carrier or vehicle for storage or administration to a patient. The invention is further directed to a treatment method, comprising administering an effective amount of the treated HSCs to a subject having a hematological disorder or other disease requiring transplantation of HSCs for treatment.

In one embodiment, the composition of treated HSCs comprises a population of human HSCs derived from umbilical cord blood, at least a portion of which are characterized as CD34$^+$CD38$^{low/-}$ HSCs having enhanced binding to P-selectin (or E-selectin). Enhanced binding to P-selectin (or E-selectin) is defined as at least 10% of the treated HSCs having fluorescence in a P-selectin binding assay (or E-selectin binding assay, respectively) which is greater than a predetermined fluorescence threshold. In another embodiment, at least 25% of the treated HSCs exceed the predetermined fluorescence threshold. In another embodiment, at least 50% of the treated HSCs exceed the predetermined fluorescence threshold. In another embodiment, at least 75% of the treated HSCs exceed the predetermined fluorescence threshold. In another embodiment, at least 90% of the treated HSCs exceed the predetermined fluorescence threshold. In another embodiment, at least 95% of the treated HSCs exceed the predetermined fluorescence threshold. The composition of human HSCs preferably is disposed in a pharmaceutically-acceptable carrier or vehicle for storage or for administration to a subject.

The predetermined fluorescence threshold in one embodiment is determined by first obtaining a sample of cells containing at least 100 $CD34^+CD38^{low/-}$ HSCs from a mononuclear fraction of ordinary umbilical cord blood (cord blood from healthy full term babies). This control (baseline) sample of HSCs is assayed using the P-selectin binding assay (or E-selectin binding assay) described elsewhere herein, or by any other P-selectin fluorescence binding assay (or E-selectin binding assay, respectively) known in the art. P-selectin (or E-selectin) binding fluorescence levels are measured for the $CD34^+CD38^{low/-}$ HSCs in the control (baseline) sample. In one embodiment, a fluorescence value is selected which exceeds the P-selectin (or E-selectin) binding fluorescence levels of at least 95% of the $CD34^+CD38^{low/-}$ HSCs in the control sample. The selected fluorescence value is designated as the predetermined fluorescence threshold against which is compared the P-selectin (or E-selectin) binding fluorescence of the treated (i.e., fucosylated) HSCs.

The present invention further contemplates a blood product produced by the method of providing a quantity or population of HSCs, at least a portion of which are $CD34^+$ and which lack or have reduced expression of protein CD38, and treating the quantity of HSCs in vitro with an $\alpha 1,3$ fucosyltransferase and a fucose donor, wherein the majority of the treated HSCs bind to P-selectin (or E-selectin). The quantity of HSCs may be derived from umbilical cord blood, but may be obtained from bone marrow or adult peripheral blood.

In general, the present invention contemplates a method wherein non-functional or suboptimally functional PSGL-1 or other selectin ligands expressed on cord blood HSCs modified by in vitro $\alpha 1,3$-fucosylation technology to correct the homing defect, which improves their use in bone marrow transplantation.

As noted above, $CD34^+$ cord blood HSCs may be defined as either $CD38^+$ (positive for CD38) or $CD38^{low/-}$ (reduced or no expression of CD38). $CD38^{low/-}$ cord blood HSCs can be identified using fluorescence techniques as described below. Cord blood HSCs are treated with a CD34-binding antibody having a fluorophore linked thereto, and with a CD38-binding antibody having a different fluorophore linked thereto. $CD34^+$ cells are defined as those HSCs which exhibit fluorescence from the anti-CD34 antibody fluorophore upon irradiation. $CD38^{low/-}$ HSCs are defined as the 30% of $CD34^+$ HSCs which have the lowest fluorescence as measured from the anti-CD38 binding antibody, or as the $CD34^+$ HSCs which have anti-CD38 binding antibody fluorescence levels of 50 units or less (as measured by a fluorescence flow cytometer as described elsewhere herein). In one embodiment, the anti-CD34 binding antibody fluorophore is FITC (fluorescein isothiocyonate) while the anti-CD38 binding antibody fluorophore is phycoerythrin (PE).

As explained previously, $CD34^+$ cells express PSGL-1 or other selectin ligands, yet a significant amount of primitive $CD34^+$ cells which are low in or lack CD38, (e.g., which comprise about 30% of the total $CD34^+$ cord blood cells), do not bind to P-selectin (or E-selectin) or bind only low amounts of P-selectin (or E-selectin, respectively). PSGL-1 is a homodimeric mucin expressed on almost all leukocytes including $CD34^+$ cells. To be functional, i.e., able to bind to P-selectin or E-selectin, PSGL-1 requires several post-translational modifications leading to formation of an $sLe^x$ group thereon, including $\alpha 1,3$-fucosylation. Insufficient $\alpha 1,3$-fucosylation, for example, results in impaired ability of naive T cells to interact with vascular selectins. In the present invention it has been discovered that the inability of cord blood derived HSCs to bind to P-selectin or E-selectin is due to inadequate $\alpha 1,3$-fucosylation of PSGL-1 or other selectin ligands. Therefore, the basis of the present invention is that the treatment of $CD34^+$ cells in vitro with an $\alpha 1,3$-fucosyltransferase (e.g., FT-VI), which also catalyzes the synthesis of the $sLe^x$ structure, will increase fucosylation of PSGL-1 or other selectin ligands and thereby correct the homing defect of the HSCs.

Fucosyltransferases which are able to transfer fucose in $\alpha 1,3$ linkage to GlcNAc are well known in the art. Several are available commercially, for example from Calbiochem. Further, at least five different types of $\alpha 1,3$ fucosyltransferases (FTIII-VII) are encoded by the human genome. These include: the Lewis enzyme (FTIII), which can transfer fucose either $\alpha (1,3)$ or $\alpha (1,4)$ to Gal$\beta$4GlcNAc or Gal$\beta$3GlcNAc respectively (Kukowska-Latallo et al., Genes Dev. 4:1288, 1990); FTIV, which forms a (1,3) linkages, which does not prefer sialylated precursors (Goelz, et al., Cell 63; 1349, 1989; Lowe, et al., J. Biol. Chem. 266; 17467, 1991); FTV (Weston, et al., J. Biol. Chem. 267:4152, 1992a) and FTVI (Weston, et al., J. Biol. Chem. 267:24575, 1992b) which form $\alpha(1,3)$ linkages, which can fucosylate either sialylated or nonsialylated precursors, and FTVII, (Sasaki, et al., J. Biol. Chem. 269:14730, 1994); Natsuka, et al., J. Biol. Chem. 269:16789, 1994) which can fucosylate only sialylated precursors.

FTIII is encoded by GDB:135717; FTIV by GDB:131563; FTV by GDB:131644; FTVI by GDB:135180; and FTVII by GDB:373982. A sixth $\alpha 1,3$ fucosyltransferase (FTIV) is encoded by GDB:9958145 (Genome Database Accession ID numbers are available from the GDB™ Human Genome Database Toronto (Ontario, Canada): The Hospital for Sick Children, Baltimore (Maryland), USA): Johns Hopkins University, 1990-. Available from Internet: URL http://www.gdb.org/). The present invention further contemplates using other, non-human $\alpha 1,3$ fucosyltransferases available and known to those of ordinary skill in the art, for example as shown in U.S. Pat. Nos. 6,399,337 and 6,461,835 which are hereby expressly incorporated by reference herein in their entireties.

As noted previously, human HSCs can be obtained for treatment with $\alpha 1,3$ fucosyltransferase, for example, by separation from the other cells in a source of umbilical cord blood, peripheral blood, or bone marrow. Various techniques may be employed to separately obtain the $CD34^+CD38^{low/-}$ stem cells alone, or in combination with $CD34^+CD38^+$ HSCs. Monoclonal antibodies are particularly useful for identifying markers (surface membrane proteins) associated with particular cell lineages and/or stages of differentiation. The antibodies may be attached to a solid support to allow for crude separation. The separation techniques employed should maximize the retention of viability of the fraction to be collected. The particular technique employed will depend upon efficiency of separation, cytotoxicity of the methodology, ease and speed of performance, and necessity for sophisticated equipment and/or technical skill.

Procedures for separation may include magnetic separation, using antibody-coated magnetic beads, and "panning"

with antibody attached to a solid matrix, e.g., plate, or other convenient technique. Techniques providing accurate separation include fluorescence activated cell sorters, which can have varying degrees of sophistication, e.g., a plurality of color channels, low angle and obtuse light scattering detecting channels, and impedance channels.

Conveniently, the antibodies may be conjugated with markers, such as magnetic beads, which allow for direct separation; biotin, which can be removed with avidin or streptavidin bound to a support; fluorochromes, which can be used with a fluorescence activated cell sorter (FACS), or the like, to allow for ease of separation of the particular cell type. Any technique may be employed which is not unduly detrimental to the viability of the remaining cells.

In one embodiment, the HSCs lacking the mature cell markers, may be substantially enriched, wherein the cells may then be separated by the FACS or other methodology having high specificity. Multi-color analyses may be employed with the FACS which is particularly convenient. The cells may be separated on the basis of the level of staining for the particular antigens. Fluorochromes, which may find use in a multi-color analysis, include phycobiliproteins, e.g., phycoerythrin and allophycocyanins, fluorescein, and Texas red, for example. Alternatively, HSCs can be treated with fucosyltransferases before separation of the desired HSCs from the unfractionated blood or bone marrow sample, for example, using total mononuclear cells from cord blood, peripheral blood, or bone marrow.

In one embodiment, the $CD34^+HSC$, including $CD34^+$ $CD38^{low/-}$ cells may be treated by adding free fucosyltransferase to the cell composition, wherein the final blood product containing the fucosylated $CD34^+CD38^{low/-}$ also contains the fucosyltransferase which was used to treat the cells. In another embodiment, the HSCs may be treated using fucosyltransferases which are bound to a support, such as magnetic beads, or any other support known by those of ordinary skill in the art, which can be separated from the cell composition after the treatment process is complete.

Methods and Results

Umbilical cord blood samples were obtained from normal full-term vaginal deliveries in accordance with a protocol approved by the Institutional Review Board of the Oklahoma Medical Research Foundation (OMRF). 70 to 100 ml of cord blood was collected per delivery. Sodium citrate was used as anticoagulant. Any appropriate method known in the art for collecting cord blood is suitable, such as the method shown in U.S. Pat. No. 6,440,010, which is expressly incorporated herein by reference in its entirety. The $CD34^+$ cells in the supernatant of the blood sample were enriched with a CD34-isolation mini-MACS kit (Miltenyi Biotec, Bergisch Gladbach, Germany). Cord blood was first mixed with an equal volume of 6% dextran 70 in 0.9% sodium chloride (McGaw, Inc., Irvine, Calif.). After sedimentation of two to three hours, the cells in the supernatant were removed, and washed once in Hanks' balanced salt solution (HBSS, Cellgro) containing 2 mM EDTA and 0.5% human serum albumin (HSA). Contaminating red blood cells were lysed in FACS Lysing solution (BD Biosciences, San Jose, Calif.). Low-density mononuclear cells (MNCs) were separated after centrifugation at 250 g over Ficoll-Hypaque (d=1.077 g/ml). $CD34^+$ cells were purified from the MNC fraction using the CD34-isolation mini-MACS kit following the manufacturer's instructions. The purity of the isolated $CD34^+$ cells was about 96% as examined by flow cytometry (FIG. 1). The following experiments were then carried out.

Verification by Flow Cytometry that $CD34^+$ Cells Isolated from Cord Blood Express PSGL-1 and the $CD34^+$ Cells are Heterogeneous.

Figure 2:
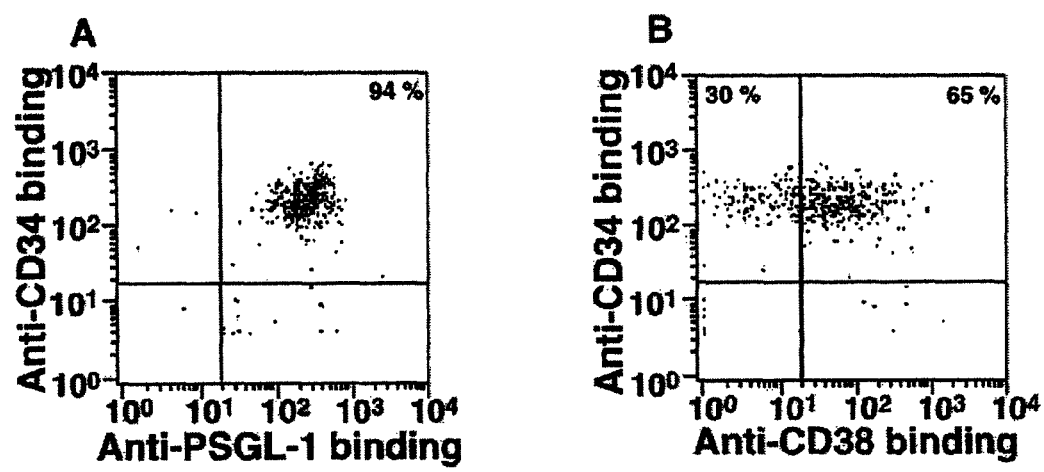
FIG. 2. A. CD34$^+$ cells isolated from cord blood express PSGL-1. B. CD34$^+$ cells consist of about 30% CD34$^+$ CD38$^{low/-}$ cells (primitive progenitors) and about 65% CD34$^+$CD38$^+$ cells. Axes are fluorescence intensity as measured by flow cytometry.
Figure 3:
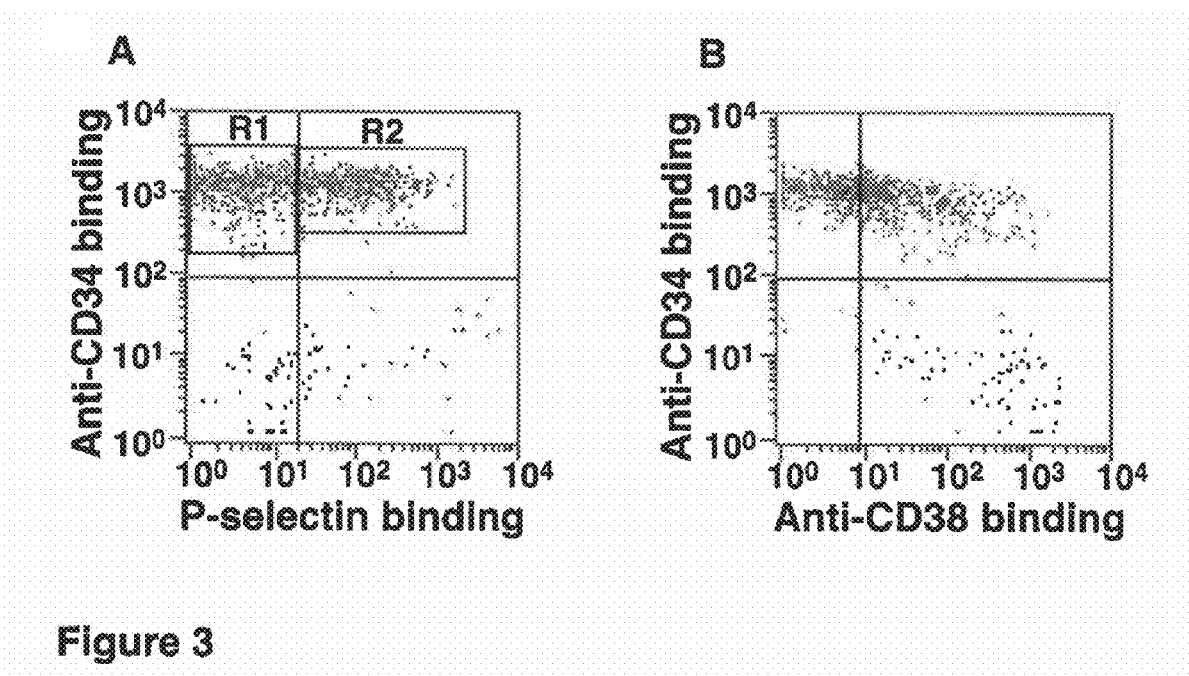
FIG. 3. A. CD34$^+$ cells are gated as P-selectin binding cells (R2) or non-P-selectin binding cells (R1). B. 24%±5% of CD34$^+$ cells from R1 region have no or reduced expression of CD38. The result is representative of four independent flow cytometry analyses and shows that significant numbers of non-P-selectin binding HSCs are CD34$^+$ and CD38$^{low/-}$.

For this purpose, triple-colored staining was used. The cells enriched by the mini-MACS sorting were incubated with anti-CD34 monoclonal antibody (mAb, clone AC136 from Miltenyi Biotec) conjugated with FITC, anti-CD38 mAb conjugated with PE (BD Pharmingen, San Diego, Calif.), and anti-PSGL-1 monoclonal antibody conjugated with Cy5 (BD Pharmingen, San Diego, Calif.) after blocking the Fc receptor with human IgG. After washing, the cells were analyzed by flow cytometry on a FACScan (Becton Dickinson). Data were collected using the CellQuest program. Light scatter-gated events were plotted on a log scale of fluorescence intensity. Virtually all $CD34^+$ cells express PSGL-1 (FIG. 2A), and about 30% of the $CD34^+$ cells have low or no expression of CD38 (FIG. 2B), representing the sub-population of primitive progenitor cells. Further, about 25% of the HSCs that do not bind to P-selectin are $CD34^+$ and $CD38^{low/-}$ (FIG. 3). These results confirm existing data.

In Vitro $\alpha$1-3-Fucosylation of PSGL-1 on Purified $CD34^+$ Cells.

Figure 4:
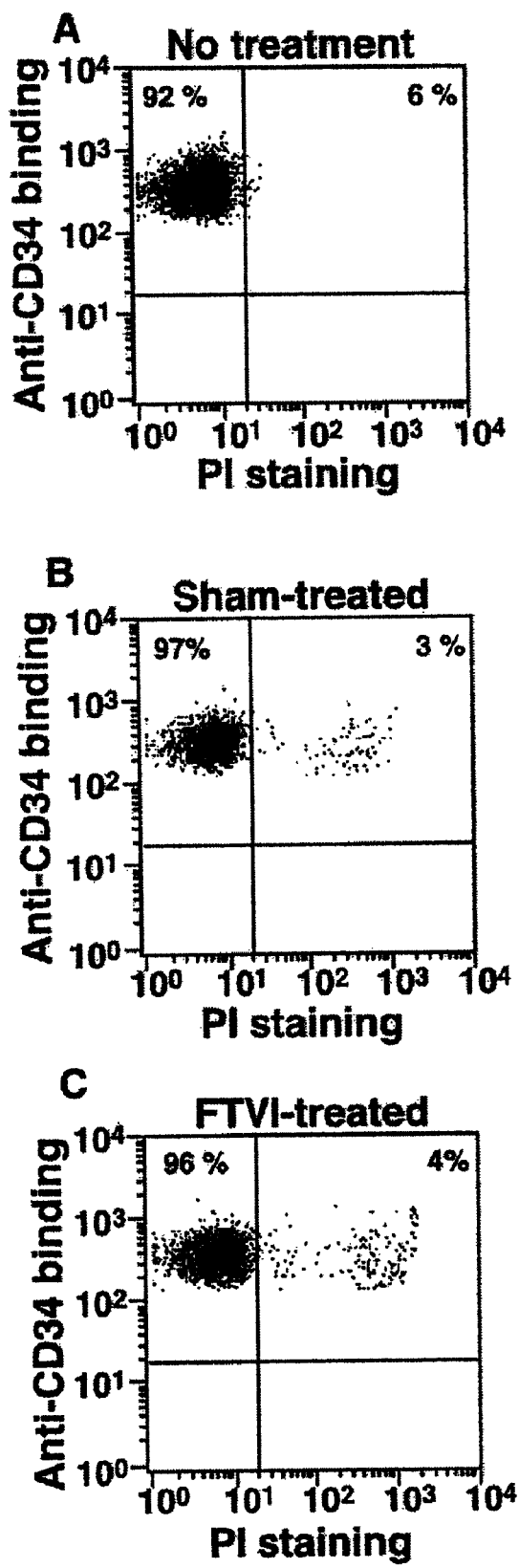
FIG. 4. Viability of cells after in vitro fucosylation as measured by propidium iodide (PI) staining. A. Cells without treatment. B. Sham-treated cells. C. FT-VI-treated cells. Axes are fluorescence intensity as measured by flow cytometry.

To introduce fucose on core 2 O-glycans attached to PSGL-1 or other selectin ligands on $CD34^+$ cells, $2-4\times10^6$ cells were treated with 1 mM guanosine diphosphate (GDP)-fucose (Calbiochem), 20 mU/mL $\alpha$1-3-fucosyltransferase VI (FT-VI) (Calbiochem), and 10 mM $MnCl_2$ in 0.5 mL HBSS/ 1% HSA for 40 minutes at 37° C., in an atmosphere containing 5% $CO_2$. This treatment produces optimal fucosylation of PSGL-1 on $CD34^+$ cells as measured by maximum P-selectin binding, yet results in minimum toxicity to $CD34^+$ cells as tested by propidium iodide staining (FIG. 4).

Measurement of Fucosylated Epitopes on $CD34^+$ Cells and Verification by Flow Cytometry that In Vitro $\alpha$1,3-Fucosylation Creates Fucosylated Epitopes on $CD34^+$ Cells.

Figure 5:
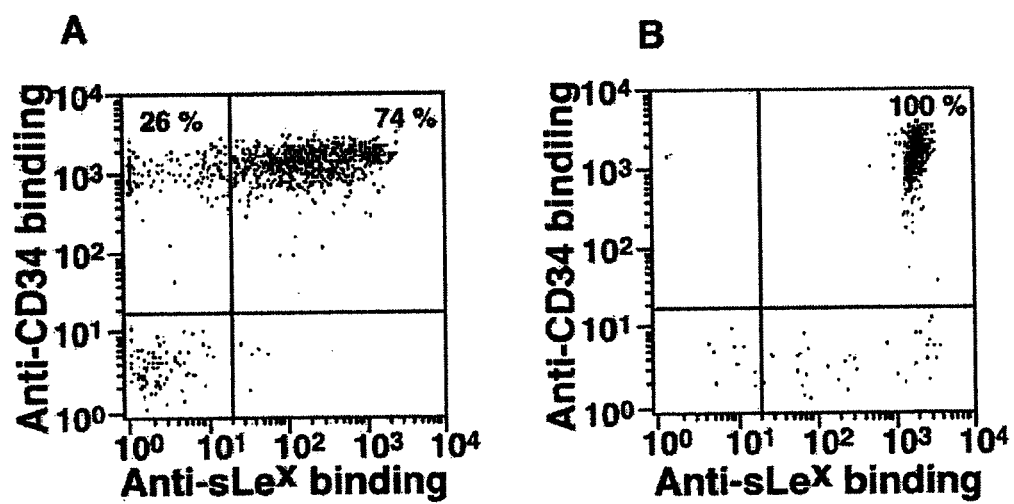
FIG. 5. A. 15% of the CD34$^+$ cells obtained from cord blood express low or no fucosylated epitopes as stained with sLe$^x$-specific monoclonal antibody HECA 452. B. In vitro α1,3-fucosylation with FT-VI and GDP-fucose dramatically increases sLe$^x$ epitopes on cord blood-derived CD34$^+$ cells. Axes are fluorescence intensity as measured by flow cytometry.

Sialyl Lewis$^x$ is a fucosylation epitope. By incubating with an anti-sLe$^x$ mAb HECA 452 (rat IgM, hybridoma from American Type Culture Collection [ATCC]), we examined the sLe$^x$ epitopes on the $CD34^+$ cells. The bound mAb was detected with FITC-conjugated goat F(ab)'2 fragments to rat IgM (Caltag). As indicated by FIG. 5A, 26% of the $CD34^+$ cells obtained from cord blood express low or no fucosylated epitopes. These data demonstrate that a subset of $CD34^+$ cells are not properly fucosylated. To investigate if in vitro $\alpha$1,3-fucosylation can create fucosylated epitopes on the $CD34^+$ cells, we stained the cells with HECA 452 after treatment of the $CD34^+$ cells with FT-VI and GDP-fucose in the presence of $Mn^{2+}$ using the method described above. We found that the in vitro $\alpha$1,3-fucosylation dramatically increased sLe$^x$ epitopes on cord blood-derived $CD34^+$ cells as indicated by HECA 452 staining (FIG. 5B).

P-Selectin Binding—Results

Verification of the Binding Profiles of Soluble P-Selectin on Cord Blood-Derived $CD34^+$ Cells.

Figure 6:
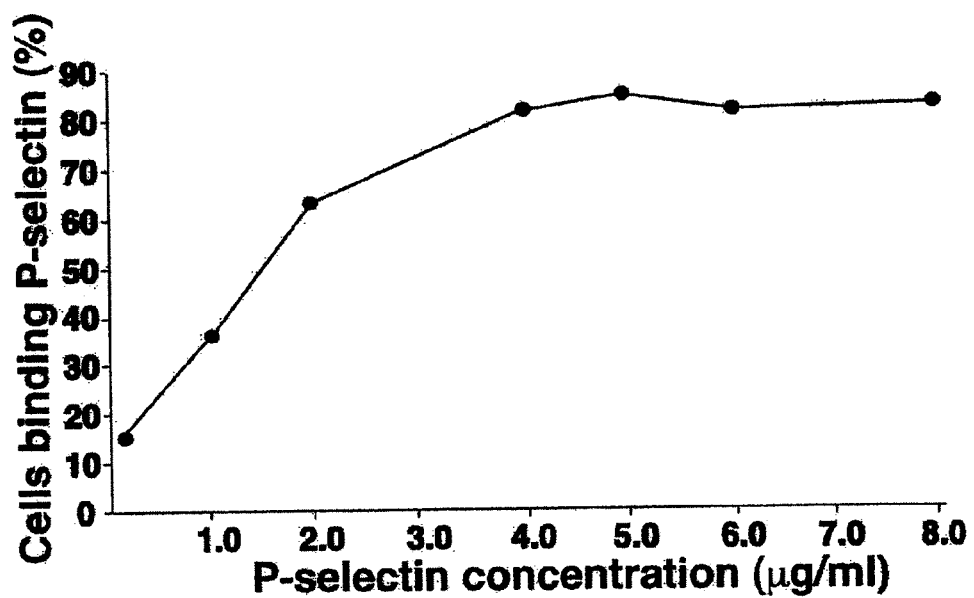
FIG. 6. Titration of soluble P-selectin binding to CD34$^+$ HSCs by flow cytometry for determining a saturating amount of P-selectin.
Figure 7:
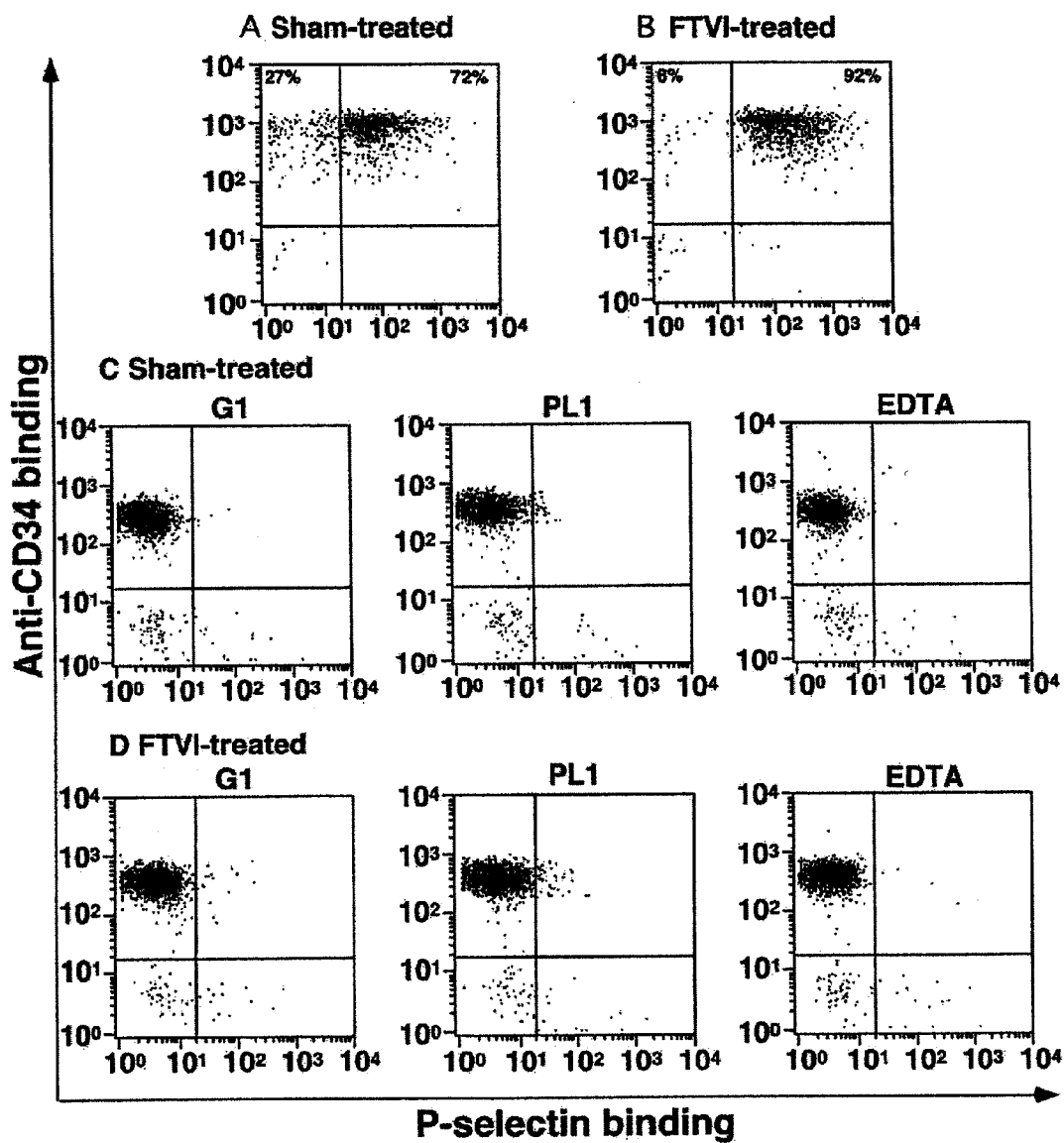
FIG. 7. Binding of a saturable concentration of soluble P-selectin to cord blood-derived CD34$^+$ cells. A. About 27% of untreated cord blood-derived CD34$^+$ cells do not bind to or have low level binding to P-selectin. B. In vitro α1,3-fucosylation converts CD34$^+$ cells which are negative or low for P-selectin binding into cells which are positive and high for P-selectin binding. C. and D. P-selectin binds to PSGL-1 on cord blood-derived CD34$^+$ cells as verified by blocking monoclonal antibodies to P-selectin (G1) and PSGL-1 (PL1). EDTA also inhibits binding, consistent with the requirement for Ca$^{2+}$ to support P-selectin binding to PSGL-1. Axes are fluorescence intensity as measured by flow cytometry.

For the P-selectin binding assay, cord blood-derived $CD34^+$ cells, after Fc receptor blocking, were incubated with anti-CD34-PE and with P-selectin isolated from human platelets. P-selectin binding was detected with FITC-labeled S12, a non-blocking mAb to human P-selectin. Incubations of the cells were performed at 4° C. for 20 min. A saturating amount of P-selectin was used in the experiments after a serial titration (FIG. 6). In control experiments, P-selectin incubations of the cells were carried out in the presence of G1, a blocking mAb to P-selectin, PL1, a blocking mAb to PSGL-1, or 10 mM EDTA, which eliminates $Ca^{2+}$-dependent selectin-ligand interactions. Flow cytometry analyses showed that about 27% of the $CD34^+$ cells (primarily comprising the CD38$^{low/-}$ cells) did not bind to P-selectin, which is consistent with previously published data (FIG. 7A) (Hidalgo, A., Weiss, L. A., and Frenette, P. S. Functional selectin ligands mediating human CD34$^+$ cell interaction with bone marrow endothelium are enhanced postnatally. Adhesion pathways mediating hematopoietic progenitor cell homing to bone marrow. J. Clin. Invest. 110:559-569. 2002). FIG. 7C showed that P-selectin bound specifically to PSGL-1 on the CD34$^+$ cells because the G1 and PL1 antibodies and EDTA abolished binding.

Demonstration by Flow Cytometry that In Vitro α1,3-Fucosylation of the Surface of CD34$^+$ Cells Increases Binding to P-Selectin.

The cord blood-derived CD34$^+$ cells were first treated with GDP-fucose and FT-VI as described above, and then stained with both anti-CD34-PE and P-selectin. The P-selectin binding was detected with FITC-labeled mAb S12. Treatment with exogenous FT-VI significantly increased binding of CD34$^+$ cells to human P-selectin (FIG. 7B). The augmented binding to P-selectin was due to the increased functional PSGL-1 on the CD34$^+$ cells after the α1,3-fucosylation because binding was blocked by antibodies G1 and PL1 and by EDTA (FIG. 7D). To find optimal conditions for in vitro α1,3-fucosylation, various incubation times and concentrations of FT-VI, GDP-fucose, and Mn were examined (data not shown). A condition (shown above) was chosen for all the experiments that produced optimal fucosylation of PSGL-1 on CD34$^+$ cells as measured by maximum P-selectin binding (FIG. 7B), yet resulted in minimum toxicity to CD34$^+$ cells as tested by propidium iodide staining (FIG. 4).

Demonstration that In Vitro α1,3-Fucosylation Increases CD34$^+$ Cell Adhesion to P-Selectin in Physiological Shear Flow.

Figure 8:
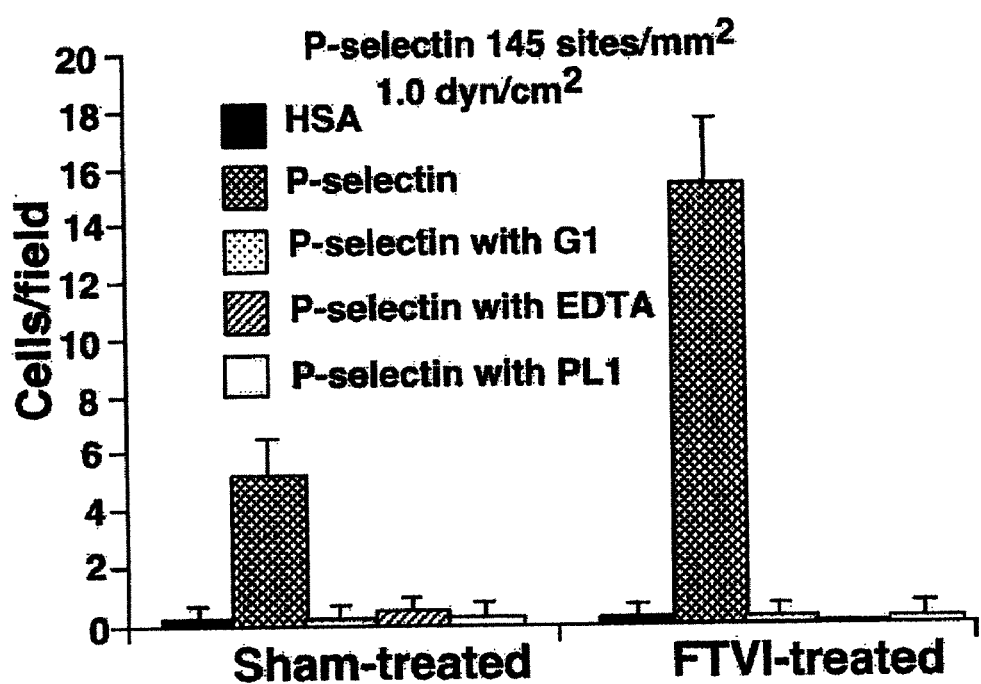
FIG. 8. Rolling of CD34$^+$ cells on human serum albumin (HSA) or on human P-selectin under shear force. Treatment of cord blood-derived CD34$^+$ cells with GDP-fucose and FT-VI significantly augments cell rolling on P-selectin in shear flow.

Cord blood-derived CD34$^+$ cells were divided into two groups for further processing. One group was incubated with GDP-fucose and FT-VI as described above, and another was treated with FT-VI without GDP-fucose (sham-treated control). The P-selectin-binding ability of the two groups of cells was compared using an in vitro flow chamber rolling assay system as described below. P-selectin isolated from human platelets was immobilized in a parallel-plate flow chamber. A P-selectin site density of 145 sites/μm$^2$ was used as measured by binding of $^{125}$I-labeled anti-P-selectin mAb S12. Sham-treated or FTVI-treated CD34$^+$ cells (10$^6$/ml in Hanks' balanced salt solution and 0.5% human albumin) were perfused over P-selectin at a wall shear stress of 1 dyn/cm$^2$. The accumulated number of rolling cells was measured with a videomicroscopy system coupled to an image analysis system. The CD34$^+$ cells rolled in a Ca$^{++}$-dependent manner by human P-selectin-PSGL-1 interactions because EDTA and antibodies G1 and PL1 abolished the rolling, and no rolling was observed on plates coated only with human serum albumin (FIG. 8). Compared to sham-treated CD34$^+$ cells, about 3-fold more FT-VI-treated CD34$^+$ cells rolled on P-selectin.

E-Selectin Binding—Results

Binding Profiles of Soluble E-Selectin to CB-Derived HSCs.

Figure 9:
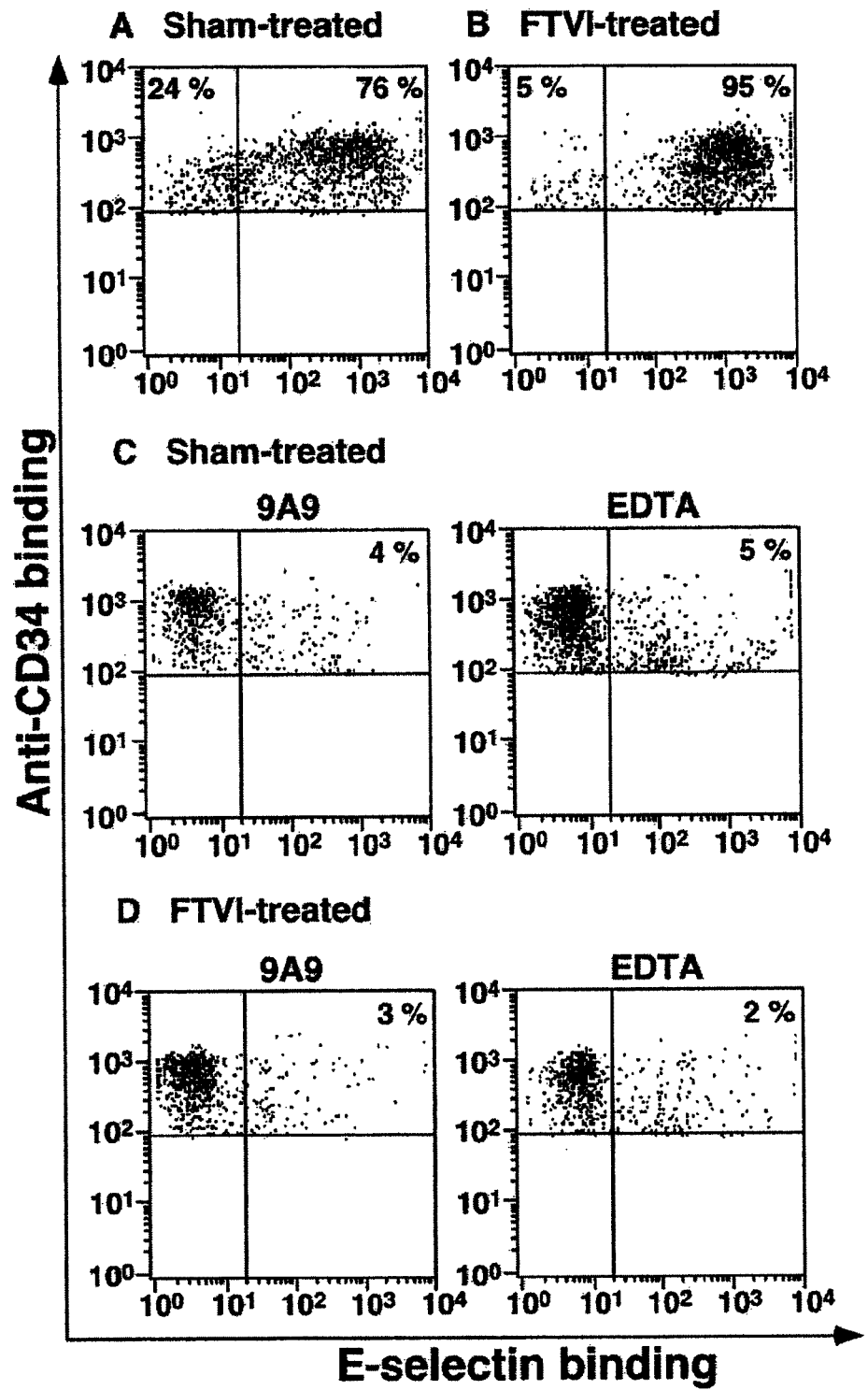
FIG. 9. Binding of a saturable concentration of soluble E-selectin to cord blood-derived CD34$^+$ cells. A. About 24% of untreated cord blood-derived CD34$^+$ cells do not bind to or have low level binding to E-selectin. B. In vitro α1,3-fucosylation converts CD34$^+$ cells which are negative or low for E-selectin binding into cells which are positive and high for E-selectin binding. C. and D. E-selectin binds to cord blood-derived CD34$^+$ cells as verified by blocking monoclonal antibodies to E-selectin (9A9). EDTA also inhibits binding. Axes are fluorescence intensity as measured by flow cytometry. The result is representative of three independent measurements.

Murine soluble E-selectin/human IgM chimera (E-selectin/IgM) was used for the fluid phase E-selectin binding assay. CD45/human IgM chimera was used as negative control. The cells were incubated with the E-selectin/Ig M after Fc receptor blocking. E-selectin binding was then detected with FITC-labeled goat anti-human IgM polyclonal antibodies. The cells were also stained with PE-labeled anti-CD34 mAb (BD Pharmingen, San Diego, Calif.). Incubations were performed at 4° C. for 20 min. A saturated amount of E-selectin was used in the experiments after a serial titration. In control experiments, stainings were carried out in the presence of 9A9, a blocking mAb to E-selectin, or 10 mM EDTA, which eliminates Ca$^{2+}$-dependent selectin-ligand interactions. Flow cytometry analyses showed that about 25% of the CD34$^+$ HSCs did not bind to E-selectin (FIG. 9A). FIG. 9C showed that the interaction of CD34$^+$ HSCs with E-selectin was specific because mAb 9A9 and EDTA abolished it.

In Vitro α1,3-Fucosylation Increases CD34$^+$ HSC Binding to E-Selectin as Measured by Flow Cytometry.

The CB-derived CD34$^+$ HSCs were divided into two groups. One group (2-4×10$^6$ cells) was incubated with 1 mM GDP-fucose, 20 mU/ml FTVI (Calbiochem), and 10 mM MnCl$_2$ in 0.5 ml HBSS/1% HSA for 40 minutes at 37° C., in an incubator containing 5% CO$_2$. Another group was incubated with FT-VI without GDP-fucose (sham-treated control). The cells were then stained with both anti-CD34 and E-selectin/IgM. After the exogenous α1,3-fucosyltransferase treatment, the binding of CD34$^+$ HSCs to E-selectin increased from 75% to 95% (FIGS. 9A and B). The augmented binding to E-selectin was specific as verified by mAb 9A9 and EDTA (FIG. 9D). The residual binding after Ab 9A9 and EDTA blocking seen in FIGS. 9C and D was non-specific because cells stained with negative control CD45/IgM had a similar profile (data not shown).

Figure 10:
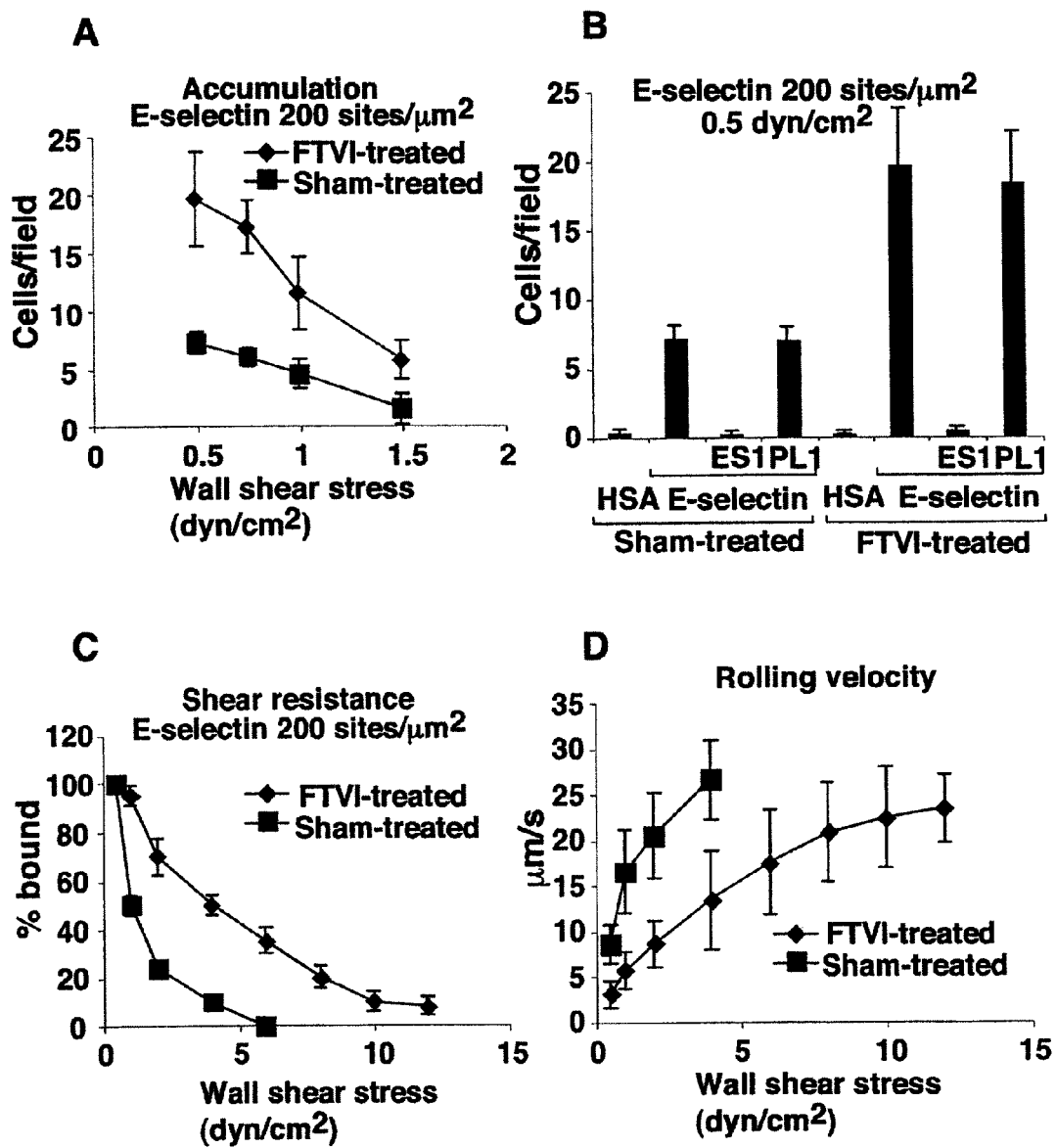
FIG. 10. In vitro fucosylation significantly augments CD34$^+$ cells rolling on human soluble E-selectin under shear forces. A and B. Treatment of CB CD34$^+$ cells with GDP-fucose and FT-VI significantly enhances the number of cells rolling on E-selectin under different shear forces. The rolling is E-selectin dependent as the cells did not roll on human serum albumin (HSA) and rolling was specifically blocked by ES1, a mAb to human E-selectin, but not by PL1, a mAb which binds to the P-selectin binding site of PSGL-1. C and D. The fucosylated CD34$^+$ cells are more resistant to shear forces and roll slower than untreated CD34$^+$ cells. The data represent the mean±SD of four independent experiments.

In Vitro α1,3-Fucosylation Increases HSC Adhesion to E-Selectin Under Physiological Shear Forces The HSCs were divide into two groups and fucosylated as described above. The E-selectin-binding ability of the two groups of cells was compared using an in vitro flow chamber rolling system. Briefly, soluble human E-selectin was immobilized in a parallel-plate flow chamber. An E-selectin site density of 200 sites/μm$^2$ was used as measured by binding of $^{125}$I-labeled anti-human E-selectin mAb ES1. Sham-treated or FT-VI-treated HSCs (10$^6$/ml in HBSS and 0.5% HSA) were perfused over E-selectin under different shear forces. The accumulated number and shear resistance of the rolling cells were measured with a videomicroscopy system coupled to an image analysis system. At shear forces examined, about 2-3 times more FT-VI-treated HSCs rolled on E-selectin compared to the sham-treated HSCs (FIGS. 10A and B). The FT-VI-treated cells also rolled with lower velocity and were more resistant to detachment by shear forces (FIGS. 10C and D). The interaction of HSCs with E-selectin was specific, as mAb ES1 abolished rolling and rolling was not observed on plates coated only with HSA (FIG. 10B). PL1, which blocks binding of P-selectin to PSGL-1, did not affect HSC rolling on E-selectin (FIG. 10B), confirming that E-selectin mediates rolling by binding to other sites on PSGL-1 or to other cell-surface ligands.

These results indicate that in vitro α1,3-fucosylation enhances physiologically-relevant rolling adhesion of CD34$^+$ cells to P-selectin and E-selectin under flow.

In Vivo Example

Fucosylated HSCs Exhibit Enhanced Engraftment in Bone Marrow In Vivo

Methods

By in vitro analyses, it has been demonstrated herein that CB HSCs treated with GDP-fucose and FTVI exhibited a significant increase in fluid-phase binding to P-selectin and E-selectin and rolled much better on P-selectin and E-selectin coated surfaces under different wall shear forces, compared with CB HSCs without fucosylation. The fucosylated CB HSCs are further shown herein to have improved homing to and engraftment in bone marrow in vivo. Nonobese diabetic severe combined immunodeficiency (NOD/SCID) mice have been well established as xenogeneic recipients for in vivo studies of human HSCs. We have compared human hematopoietic engraftment in NOD/SCID mice transplanted with CB HSCs with or without fucosylation.

Male and female pathogen-free (NOD/SCID) mice (The Jackson Laboratory), 4-5 weeks of ages, were used as recipients. The mice were irradiated (230 rad) 2 or 3 hours before intravenous injections of FTVI-treated (fucosylated) or sham-treated (treated with FTVI but without GDP-fucose) CB HSCs ($8 \times 10^6$/mouse in 300 µl saline) respectively. Control mice each received 300 µl saline without CB HSCs.

Six weeks after transplantation, the mice were bled and sacrificed. Bone marrow cells were isolated from both femora and filtered through a 100-mm mesh filter to remove debris. After lysis of red blood cells, the bone marrow nucleated cells from each mouse were resuspended in HBSS at a concentration of $1 \times 10^6$/ml. The engraftment was analyzed by both flow cytometry and human hematopoietic progenitor assays. For flow cytometry, bone marrow nucleated cells were incubated with a Cy5-conjugated anti-human CD45 mAb (BD Pharmingen, San Diego, Calif.).

For human hematopoietic progenitor assays, $1 \times 10^5$ bone marrow nucleated cells per 35-mm culture dish were plated into MethoCult H4433 media (Stem Cell Technologyies, Vancouver, Canada) in duplicate and incubated at 37° C., 5% $CO_2$. Total colonies, burst-forming units-erythroid (BFU-E), colony-forming units-granulocyte/macrophage (CFU-GM), and colony-forming units-granulocyte/megakaryocyte/macrophage (CFU-GEMM) were counted on day 14 of culture and analyzed. The human origin of the colonies was confirmed by flow cytometry analysis of cells collected from different colonies stained with mAbs to human CD45 for myeloid cells and glycophorin A for erythroid cells, respectively.

Results

Figure 11:
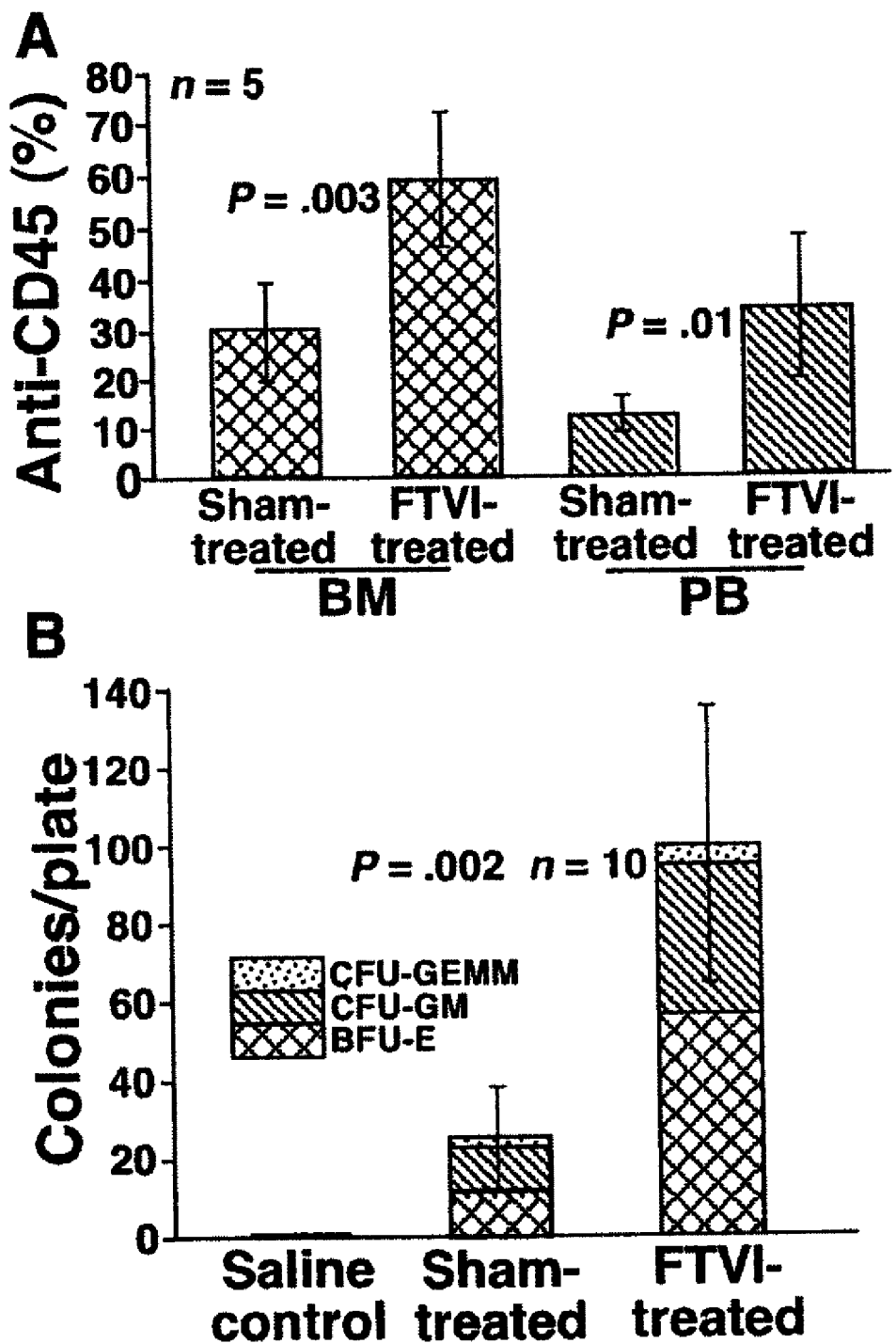
FIG. 11. Fucosylated CB HSCs exhibit enhanced engraftment in bone marrow of sublethally irradiated NOD/SCID mice. Bone marrow (BM) or peripheral blood (PB) from mice 6 weeks after transplantation with 8×10$^6$ sham-treated or FTVI-treated CB cells were analyzed for engraftment of human-derived hematopoietic cells. (A) Flow cytometry analysis of BM and PB cells stained with a mAb to the human pan-leukocyte marker CD45 demonstrated a doubling of human-derived cells in mice transplanted with fucosylated CB cells. (B) Compared with mice transplanted with CB cells without fucosylation, BM cells from mice transplanted with fucosylated CB cells contain significantly more human colony-forming progenitors, which include BFU-E, CFU-GM, and CFU-GEMM, as demonstrated by human hematopoietic progenitor assays. Bone marrow of control mice injected with saline only produced no colonies, confirming the specificity of the assay.

The irradiated NOS/SCID mice that received fucosylated CB HSCs had 2-3 fold more CD45 positive human-derived hematopoietic cells in bone marrow and peripheral blood than mice that received sham-treated CB HSCs, as analyzed by flow cytometry (FIG. 11A). The significantly improved engraftment of human hematopoietic progenitors in bone marrow of mice transplanted with fucosylated cells was multilineage as demonstrated by the increases of BFU-Es, CFU-GMs, and CFU-GEMMs (FIG. 11B). Of note, the sizes of the colonies derived from CB HSCs were not significantly different in either recipient group (data not shown), indicating that fucosylation did not change the growth potential of the CB progenitors. Thus, the in vivo study demonstrates that the FTVI-treated CB HSCs have much higher potential to home to and engraft in bone marrow of NOD/SCID mice than the sham-treated cells do. These results show that the HSCs of the present invention will have enhanced bone marrow engraftment in humans.

Utility

The fucosylated HSCs described herein may be used in a variety of ways. For example, since the cells are naive (primitive), they can be used to fully reconstitute the bone marrow of an irradiated subject and/or an individual subjected to chemotherapy.

Among the conditions which can be treated by administration of hemopoietic stem cells according to the present invention are leukemias and lymphomas such as chronic myelocytic (myelogenous) leukemia (CML), juvenile chronic myelogenous leukemia (JCML), acute myelocytic leukemia (AML), acute lymphocytic leukemia (ALL), malignant lymphoma, multiple myeloma, aplastic anemia gravis, myelodysplastic syndrome (MDS), and autoimmune diseases, for example.

Other diseases that may be treated with the treated HSCs of the present invention are: Gunther's disease, Hunter syndrome, Hurler syndrome, neuroblastoma, non-Hodgkin's lymphoma, Wiskott-Aldrich syndrome, X-linked lymphoproliferative syndrome, and solid tissue tumors, such as breast cancer.

In these treatments, populations of these treated HSCs can be given to a patient whose marrow has been destroyed by ablative therapy.

The cells of the present invention can be administered by intravenous injection, for example, or by any other appropriate method known by those of ordinary skill in the art. In methods for treating a host afflicted with a disease or condition, a therapeutically effective amount of HSCs is that amount sufficient to reduce or eliminate the symptoms or effects of the disease or condition. The therapeutically effective amount administered to a host will be determined on an individual basis and will be based, at least in part, on consideration of the individual's size, the severity of symptoms to be treated, and the results sought. Thus, a therapeutically effective amount can be determined by one of ordinary skill in the art of employing such practice in using no more than routine experimentation. For detailed information on HSC transplantations, "*Hemopoietic Stem Cell Transplantation, Its Foundation and Clinical Practice*" [Modern Medicine, Special Issue, 53, 2, 1998] can be consulted and the descriptions given there are expressly incorporated herein by reference in their entirety.

In preparing the dosage of fucosylated stem cells to be administered, a variety of pharmaceutically acceptable carriers can be utilized. The carrier, diluent or vehicle may contain a buffering agent to obtain a physiologically acceptable pH, such as phosphate-buffered saline, and/or other substances which are physiologically acceptable and/or are safe for use. In general, the material for intravenous injection in humans should conform to regulations established by the Food and Drug Administration, which are available to those in the field. Pharmaceutically-acceptable carriers may be combined, for example, in a 1 volume:1 volume ratio, with the treated HSC composition. The carrier may be for example, M199 or RPMI 1640 medium. Furthermore, in preparing said dosage form, various infusions in common use today can also be employed. In one embodiment, the dose amount conventionally used in the transplantation of HSCs can be employed. The dosage may be, for example, about $0.01\text{-}10 \times 10^8$ treated MNCs/kg of weight (which includes treated $CD38^{low/-}$ HSCs or other treated HSCs as defined elsewhere herein) of the patient, or more, or less where appropriate.

As described herein, the present invention contemplates a method of treating HSCs, comprising providing a quantity of HSCs, at least a portion of the HSCs lacking or having reduced expression of surface protein CD38, and treating the quantity of HSCs in vitro with an α1,3-fucosyltransferase and a fucose donor forming treated HSCs, wherein the treated HSCs have enhanced binding to P-selectin or E-selectin. In one embodiment, the portion of HSCs lacking or having reduced expression of surface protein CD38 has reduced bone marrow homing ability. The HSCs may be derived from human umbilical cord blood, and may be an unfractionated quantity of human umbilical cord blood. Alternatively, the HSCs may be derived from peripheral blood, and may be an unfractionated quantity of peripheral blood. Alternatively, the HSCs may be derived from bone marrow, and may be an unfractionated quantity of bone marrow. The portion of HSCs lacking or having reduced expression of surface protein CD38 comprises PSGL-1 or other structures which have unfucosylated glycans or unfucosylated O-glycans. In the present method, the portion of HSCs lacking or having reduced expression of surface protein CD38 may comprise PSGL-1 having core-2 O-glycans comprising NeuAc$\alpha$2,3 Gal $\beta$1,4 GlcNAc and which are absent a fucose in $\alpha$1,3 linkage to the GlcNAc or which comprise other glycans which lack proper fucosylation. In one embodiment, at least 50% of the treated HSCs have P-selectin binding fluorescence which exceeds a predetermined fluorescence threshold in a P-selectin binding assay or E-selectin binding fluorescence which exceeds a predetermined fluorescence threshold in an E-selectin binding assay (as described elsewhere herein). In the present method, the $\alpha$1,3 fucosyltransferase may be $\alpha$1,3 fucosyltransferase IV, $\alpha$1,3 fucosyltransferase VI, or $\alpha$1,3 fucosyltransferase VII. Further, the fucose donor may be GDP-fucose.

The present invention further contemplates a composition of HSCs which comprises CD34$^+$ HSCs derived from umbilical cord blood and lacking or having reduced expression of surface protein CD38, wherein at least 10% of the CD34$^+$ HSCs bind to P-selectin (or E-selectin), and a pharmaceutically-acceptable carrier. In the composition, in alternative embodiments, at least 25%, 50%, 75%, 90%, or 95% of the CD34$^+$ HSCs bind to P-selectin (or E-selectin).

The present invention also contemplates treating a subject with a hematological disease or other condition requiring a transplantation of HSCs by administering a quantity of the composition of treated HSCs described herein to the subject having a hematological disease or other condition requiring a transplantation of HSCs. The hematological disease may be, for example, acute lymphocytic leukemia, acute myelogenous leukemia, myelodispasia, chronic myelogenous leukemia, juvenile chronic myelogenous leukemia, or sickle cell anemia.

Furthermore, the present invention contemplates a blood product comprising a population of human HSCs comprising cells characterized as CD34$^+$CD38$^{low/-}$, wherein at least 10% of the CD34$^+$CD38$^{low/-}$ HSCs bind to P-selectin or E-selectin. In the blood product, in alternative embodiments, at least 25%, 50%, 75%, 90%, or 95% (or any percentage inclusive) of the CD34$^+$CD38$^{low/-}$ HSCs bind to P-selectin or E-selectin. In the blood product, the human HSCs may be derived from human umbilical cord blood, adult peripheral blood, or bone marrow. The blood product may also comprise a pharmaceutically acceptable carrier or vehicle, and may also comprise a free fucosyltransferase or a fucosyltransferase bound to a support.

The present invention also contemplates a blood product produced by the method comprising providing a quantity of HSCs, at least a portion of the HSCs lacking or having reduced expression of surface protein CD38, and treating the quantity of HSCs in vitro with an $\alpha$1,3-fucosyltransferase and a fucose donor to produce treated HSCs, wherein at least 10% of the treated HSCs bind to P-selectin or E-selectin. In an alternative embodiment at least 25%, 50%, 75%, 90%, or 95% (or any percentage inclusive) of the treated HSCs of the blood product bind to P-selectin or E-selectin. In the blood product, the quantity of HSCs may be derived from human umbilical cord blood, peripheral blood, or bone marrow.

While the invention has been described above in connection with various embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the previous examples will serve to illustrate the practice of this invention, it being understood that the particulars shown are by way of example and for purposes of illustrative discussion of the present invention only and are presented in the cause of providing what is believed to be the most useful and readily understood description of procedures as well as of the principles and conceptual aspects of the invention.

All references, patents and patent applications cited herein are hereby incorporated herein by reference in their entireties.

Changes may be made in the construction and the operation of the various compositions and products described herein or in the steps or the sequence of steps of the methods described herein without departing from the spirit and scope of the invention as described herein.

What is claimed is:

1. A composition of fucosylated cord blood-derived CD34$^+$ cells; comprising:
   cord blood-derived CD34$^+$ cells which lack or have reduced expression of surface protein CD38, wherein said fucosylated cord blood-derived CD34$^+$ cells are produced by treating said cord blood-derived CD34$^+$ cells in vitro with an $\alpha$1,3 fucosyltransferase in the presence of a fucose donor, and wherein at least 10% of the fucosylated cord blood-derived CD34$^+$ cells have enhanced binding to P-selectin in comparison to the cord blood-derived CD34$^+$ cells before treatment with the $\alpha$1,3 fucosyltransferase in the presence of a fucose donor.

2. The composition of claim 1 wherein at least 25% of the fucosylated cord blood-derived CD34$^+$ cells bind to P-selectin or E-selectin in comparison to the cord blood-derived CD34$^+$ cells before treatment with the $\alpha$1,3 fucosyltransferase.

3. The composition of claim 1 wherein at least 50% of the fucosylated cord blood-derived CD34$^+$ cells bind to P-selectin or E-selectin in comparison to the cord blood-derived CD34$^+$ cells before treatment with the $\alpha$1,3 fucosyltransferase.

4. The composition of claim 1 wherein at least 75% of the fucosylated cord blood-derived CD34$^+$ cells bind to P-selectin or E-selectin in comparison to the cord blood-derived CD34$^+$ cells before treatment with the $\alpha$1,3 fucosyltransferase.

5. The composition of claim 1 wherein at least 90% of the fucosylated cord blood-derived CD34$^+$ cells bind to P-selectin or E-selectin in comparison to the cord blood-derived CD34$^+$ cells before treatment with the $\alpha$1,3 fucosyltransferase in the presence of a fucose donor.

6. The composition of claim 1 wherein at least 95% of the fucosylated cord blood-derived CD34$^+$ cells bind to P-selectin or E-selectin in comparison to the cord blood-derived CD34$^+$ cells before treatment with the $\alpha$1,3 fucosyltransferase.

7. The composition of claim 1 wherein the fucosylated cord blood-derived CD34$^+$ cells are disposed within a pharmaceutically acceptable carrier, diluent, or vehicle.

8. The composition of claim 1 wherein the fucosylated cord blood-derived CD34$^+$ cells are human.

9. The composition of claim 1 further comprising the $\alpha$1,3-fucosyltransferase as a free fucosyltransferase or as a fucosyltransferase bound to a support.

10. A blood product produced by the method comprising:
    providing cord blood-derived CD34$^+$ stem cells which lack or have reduced expression of surface protein CD38, and which comprise P-selectin glycoprotein ligand-1 (PSGL-1) having core-2 O-glycans comprising NeuAcα2,3 Galβ1,4 GlcNAc which lack fucose in α1,3 linkage to the GlcNAc, and which have impaired binding to E-selectin or P-selectin; and treating said cord blood-derived CD34+ cells in vitro with an α1,3-fucosyltransferase and a fucose donor to produce fucosylated cord blood-derived CD34+ cells which have enhanced binding to P-selectin or E-selectin, and wherein the fucosylated cord blood-derived CD34+ cells are disposed within a pharmaceutically acceptable carrier, diluent, or vehicle.

11. The blood product of claim 10 wherein the cord blood-derived CD34+ cells are human.

12. The blood product of claim 10 further comprising the α1,3-fucosyltransferase as a free fucosyltransferase or as a fucosyltransferase bound to a support.

* * * * *

UNITED STATES PATENT AND TRADEMARK OFFICE
CERTIFICATE OF CORRECTION

Page 1 of 1

PATENT NO. : 8,084,255 B2
APPLICATION NO. : 12/707481
DATED : December 27, 2011
INVENTOR(S) : Lijun Xia and Rodger P. McEver It is certified that error appears in the above-identified patent and that said Letters Patent is hereby corrected as shown below:

In the Specification:
Column 8, line 26: After "which forms" delete "a" and replace with -- α --

In the Claims:
Column 17, line 1, Claim 10: After "Gal" delete "131," and replace with -- β1, --

Signed and Sealed this
Fourteenth Day of February, 2012

David J. Kappos
*Director of the United States Patent and Trademark Office*